United States Patent

Barri et al.

[11] Patent Number: 5,210,364
[45] Date of Patent: May 11, 1993

[54] PROCESS FOR THE PREPARATION OF BRANCHED OLEFINS

[75] Inventors: Sami A. I. Barri, Berkshire; David A. Kidd, Fleet, both of England

[73] Assignee: The British Petroleum Co., p.l.c., London, England

[21] Appl. No.: 790,294

[22] Filed: Nov. 7, 1991

[30] Foreign Application Priority Data

Nov. 8, 1990 [GB] United Kingdom ............... 9024342

[51] Int. Cl.⁵ .............................................. C07C 1/00
[52] U.S. Cl. ................................ 585/640; 585/639
[58] Field of Search ............................. 585/639, 640

[56] References Cited

U.S. PATENT DOCUMENTS

| | | | |
|---|---|---|---|
| 4,506,106 | 3/1985 | Hsia et al. | 585/640 |
| 4,543,435 | 9/1985 | Gould | 585/530 |
| 4,550,217 | 10/1985 | Graziani et al. | |
| 4,579,999 | 4/1986 | Gould et al. | 585/640 |
| 4,590,320 | 5/1986 | Sapre | |
| 4,684,757 | 8/1987 | Avidan et al. | 585/640 |
| 4,851,606 | 7/1989 | Ragonese et al. | |
| 5,047,141 | 9/1991 | Chu | 585/640 |

FOREIGN PATENT DOCUMENTS

| | | |
|---|---|---|
| 65400 | 11/1982 | European Pat. Off. . |
| 88965 | 9/1983 | European Pat. Off. . |
| 2171718 | 9/1986 | United Kingdom . |

Primary Examiner—Patrick P. Garvin
Assistant Examiner—E. D. Irzinski
Attorney, Agent, or Firm—D. P. Yusko; D. J. Untener; L. W. Evans

[57] ABSTRACT

A process for the production of olefins which comprises passing an oxygenate-containing feedstock over a zeo type catalyst at a temperature greater than 200° C. characterized in that the oxygenate-containing feedstock comprises $C_3$ and/or $C_4$ olefins and as oxygenate methanol formaldehyde and/or dimethylether, the molar ratio of olefin to oxygenate being greater than 1:20 and the zeo type catalyst being of TON-type structure.

8 Claims, 1 Drawing Sheet

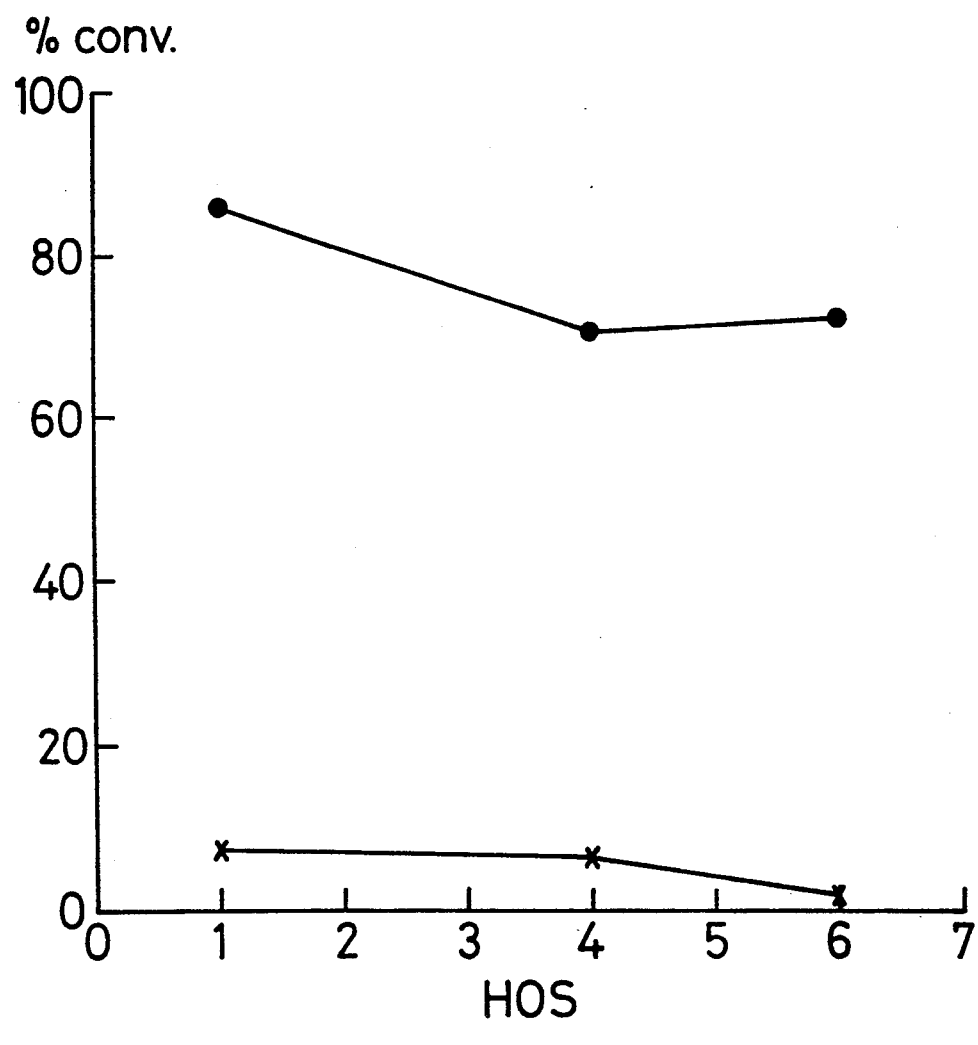

PROCESS FOR THE PREPARATION OF BRANCHED OLEFINS

The present invention relates to a catalytic process for the production of branched olefins by utilising a zeolite catalyst in the conversion of oxygenates, especially methanol, in the presence of olefins.

It is known from EP-A-65400 that a zeolite of TON-type structure (referred to in that document as Nu-10) is able to convert methanol into olefins. However, experiments have shown that this reaction is inefficient as the catalyst deactivates after a short period of time.

U.S. Pat. No. 4,684,757 also describes a methanol to olefins process. In this process, ethene and/or propene are amongst the products produced, and these are then recycled to the reaction. Although zeolite ZSM-5 is the preferred catalyst for the reaction disclosed in U.S. Pat. No. 4,684,757, other zeolites are also listed: these zeolites are ZSM-11, ZSM-12, ZSM-22, ZSM-23, ZSM-35, ZSM-38, ZSM-45 and ZSM-50. ZSM-22 is of TON-type structure. In fact, ZSM-22 would not be a suitable catalyst for the process of U.S. Pat. No. 4,684,757: as stated above, the catalyst deactivates after a short period of time when using an initial feed of methanol.

The conversion of methanol to olefins over ZSM-5 is very well known. In addition to U.S. Pat. No. 4,684,757 described above, the following documents are of interest. U.S. Pat. No. 4,543,435 describes a process in which ethene is recycled in an amount of up to 20 parts by weight ethene to 100 parts by weight methanol. U.S. Pat. No. 4,579,999 discloses a similar process wherein gasoline range olefins of $C_5$ and above are recycled to the reaction process. Such processes using ZSM-5 convert methanol into a wide spectrum of olefinic products plus gasoline, the precise product composition depending of course on the reaction conditions used. Thus, U.S. Pat. No. 4,543,435 at column 4 lines 43 onwards gives yields obtained in a fluidised bed using ZSM-5 catalyst. The major products obtained are $C_5$ and higher gasoline-range hydrocarbons, with other products over a range of carbon numbers also being produced. Ethene recycle makes almost no difference to the product distribution.

We have now found a method for the very selective production of $C_4/C_5$ olefins. This method uses a feed containing methanol, formaldehyde and/or dimethyl ether, together with a $C_3$ and/or $C_4$ olefin, and a TON-type zeolite as a catalyst. Unlike prior art methods of using TON-type catalysts, catalyst deactivation is significantly retarded. The product spectrum obtained is completely different from that obtained using ZSM-5.

Accordingly, the present invention provides a process for the production of olefins which comprises passing an oxygenate-containing feedstock over a zeo type catalyst at a temperature greater than 200° C. characterised in that the oxygenate-containing feedstock comprises $C_3$ and/or $C_4$ olefins and as oxygenate methanol formaldehyde and/or dimethylether, the molar ratio of olefin to oxygenate being greater than 1:20 and the zeo type catalyst being of TON-type structure.

The process provides a product which is rich in branched olefinic hydrocarbons.

Throughout this specification and claims, the term oxygenate should be understood to mean methanol, formaldehyde and/or dimethylether. The feedstock comprises oxygenate and a proportion of $C_3$ and/or $C_4$ olefinic hydrocarbons. The oxygenate and $C_3/C_4$ olefins are present in the feedstock in molar ratio of greater than 1 mole olefin to 20 moles oxygenate, preferably greater than 1 mole olefin to 10 moles oxygenate, especially greater than 1 mole olefin to 5 moles oxygenate, most preferably greater than 1 mole olefin to 4 moles oxygenate. Preferably the feedstock contains at least 1 mole oxygenate to 20 moles olefin. The ratio could be chosen suitably according to the conditions and catalyst composition employed to maximise the production of isobutene and methylbutenes. The preferred oxygenate is methanol.

Processes for the preparation of olefins wherein ethene and/or propene are present along with methanol are well known, especially when using zeolite ZSM-5 as catalyst. In such processes, the initial feed is methanol, and the olefins are generally introduced to the reaction chamber as a recycled by-product. It therefore can be assumed that the concentration of such olefins in the process is low. In contrast, the $C_3-C_4$ olefins of the present process are introduced as co-reactants in relativsly high concentrations.

The feedstock may enter the reaction chamber as a single pre-mix. Equally suitable, the components may be fed in separately and mixed thereafter in the reaction chamber. The feedstock may if desired be diluted with, for example, water, alkanes or an inert gas.

A code consisting of three capital letters has been adopted for each known structure type following the recommendations by IUPAC on zeolite nomenclature ("Chemical Nomenclature and Formulation of Compositions of Synthetic and Natural Zeolites", IUPAC, yellow booklet, 1978). TON-type structures are disclosed in the Atlas of Zeolite Structure Types by Meier W. M. and Olsen D. H., 1987 distributed by Polycrystal Book Service, Pittsburgh U.S.A. Such TON-type structures have uni-dimensional, non-intersecting channels with ten-membered ring openings of about 6 Å in diameter.

The reaction may be carried out over zeo-type catalysts that have the TON-type structure e.g. aluminosilicates, gallosilicates, zincosilicates, borosilicates, titanosilicates etc or their germanate counterparts. Preferably, the zeo-type catalyst is an alluminosilicate.

For simplicity, the specification relates to the preparation and use of aluminosilicates. It should of course be understood that the additional aforementioned TON-type structures may also be used and can be prepared in an analogous manner.

Zeolites having TON-type structure are also known by the names Theta-1 which is disclosed in our European patent 57049, Nu-10 which is disclosed in the European patent 65400 and ZSM-22 which is disclosed in the Canadian Patent No 1202941.

The zeolite is suitably prepared from an initial mixture containing a source of silica, a source of alumina, a source of alkali metal(s), water and either an organic nitrogen containing base, as discussed in the European patents above or an inorganic nitrogen base as discussed in EP-A-104800.

The zeolite may be prepared by forming a mixture of all the reactants as described in the above documents. The mixture is then crystallised at a temperature above 70° C., preferably between 100° and 200° C. for suitably at least 2 hours, preferably 6 to 240 hours. The optimum crystallisation period can vary and may depend upon such factors as the temperature, pH and gel composition. Preferably, the source of silica is an amorphous silica sol which is diluted with water. It is preferred that the silica source is added to the other reagents in such a way as to commence gelation at a relatively high pH.

The zeolite may vary in composition depending on the method of synthesis eg the Si/Al ratio of the product may be varied by controlling the Si/Al ratio of the hydrogel precursor or by varying the OH/Si ratio.

The zeolite produced contains cations which, depending upon the precise synthesis method used, may be hydrogen, aluminium, alkali metals, organic nitrogen containing cations or any combination thereof.

The zeolite is preferably used in the present process in the hydrogen form. The hydrogen form may be achieved by, in the case of organic containing zeolite, calcination to remove the organics followed by either ammonium ion exchange followed by calcination, Proton exchange with an acid solution or a combination of both. In the case of a zeolite synthesised in the absence of organic nitrogen containing compound the hydrogen form could, if desired, be prepared by either direct ammonium ion exchange followed by calcination or proton exchange with acid solution or a combination of both. The preparation of the hydrogen form of the zeolite may vary to maximise the production of isobutene and methylbutenes. If so desired, the hydrogen form of the zeolite also may be partially or completely exchanged or impregnated with a metal such as Ga or Mg and used in the present process.

The zeolite may be modified to alter its acidity or shape selectivity in such a way to improve the catalytic performance. The modifications may include a calcination regime, st sam treatment, chemical treatment e.g. with dealuminating agent e.g. $SiCl_4$, EDTA, etc, aluminating agent e.g. sodium aluminate, $AlCl_3$ etc, inclusion of phosphorous compound, Lewis base, HF etc. A combination of treatments may also be carried out. The zeolite may be treated during the preparation of the H-form or be carried out on the H-form.

The zeolite may, if desired, be bound in a suitable binding material either before or after impregnation or after exchange with a metal compound. The binder may suitably be one of the conventional alumina, silica, clay, or aluminophosphate binders or a combination of binders.

The process according to the invention is carried out at a temperature in excess of 200° C., preferably 250° to 600° C. and may be carried out at reduced or elevated pressure, relative to atmospheric pressure. Suitably, a pressure of from 0.1-100 bar absolute, preferably from 0.5-10 bar absolute and most preferably from 2-10 bar absolute may be used.

The feedstock is fed into the reaction chamber either with or without diluents e.g. water, steam, alkanes or inert gas at a rate of suitably 0.1-1000 weight hourly space velocity (WHSV). Preferably, the WHSV is at least 2, more preferably at least 5, especially at least 10. WHSV's of up to 500, especially up to 100, are preferred. For the purposes of the present invention, it is understood that weight hourly space velocity is defined as the weight of olefin and oxygenate fed per weight of catalyst per hour. In addition, the mole % of any diluent gas present in the feed may be up to 90%, preferably up to 70%, most preferably up to 60%. If a diluent is present, it is preferably present in an amount of at least 5%.

It is well known that zeolites and similar molecular sieves tend to concentrate the reactants and thus promote bimolecular reactions. Zeolites such as those having structures of the MFI or MEL types tend to produce high levels of oligomers, naphthenes, aromatics and alkanes all of which are produced due to the promotion of bimolecular reactions. In this invention it has been found that the formation of heavy hydrocarbons can be reduced by a combination of using a molecular sieve having TON-type structure and optimising the WHSV or the contact time of the reaction. The optimum WHSV would be dependent on the other operating conditions and the catalyst composition and pretreatment. The relative concentration of the reactants can be optimised by adjusting the hydrocarbons to oxygenates ratio. In addition the contact time is optimised at constant WHSV by dilution with inert gas or less reactive gas than the reactants.

The process may be carried out in any suitable reactor, for example a fixed bed, a fluid bed, a slurry reactor or a continuous catalyst regeneration reactor.

The product of the process includes branched olefinic hydrocarbons, rich in isobutene and methylbutenes. A small amount of by-products e.g. methane, ethane, ethene and linear olefins are also present.

The products of the present process may be utilized as reactants in a second process, in particular, the etherification of branched olefins with an alcohol. The final products of the overall two-step process may suitably be methyl tertiarybutylether/tertiary amylmethylether mixtures and gasoline range hydrocarbons.

Alternatively, the products of the present invention may be further reacted to increase the degree of branching. Linear olefins produced may be isomerised to produce additional branched olefins. Oligomerisation of the small olefinic hydrocarbons may suitably produce highly branched higher olefins. Furthermore, alkylation of the linear olefins may produce aliphatic hydrocarbons suitable for gasoline blending or if so desired, aromatisation of the linear olefins may provide aromatic hydrocarbons suitable for gasoline blending.

The process will now be described with reference to the following examples.

EXAMPLE 1 SYNTHESIS OF THETA-1 ZEOLITE

Theta-1 was synthesised using ammonia as the templating agent. Sodium aluminate (30 g, ex BDH, 40 wt % $Al_2O_3$, 30 wt % $Na_2O$ and 30 wt % $H_2O$) and sodium hydroxide (15.68 ex BDH) were dissolved in distilled water (240 g). Ammonia solution (14008, SG 0.90 containing 25% $NH_3$) was added with gentle mixing. Ludox AS40 (Trade Mark) (12008) which contained 40 wt % silica was added over fifteen minutes with stirring to maintain a homogeneous hydrogel. The molar composition of the hydrogel was:

2.9 $Na_2O$:175 $NH_3$: 1.0 $Al_2O_3$:68 $SiO_2$:950 $H_2O$

The mixture was then loaded into a 5 liter Parr autoclave and crystallised at 175° C. for 25 hours under autogeneous pressure whilst mixing by a mechanical stirring action. At the end of the crystallisation period the autoclave was cooled, and the product filtered, washed and dried in an air oven at 100° C. The crystallinity and the purity of the zeolite were determined by X-ray powder diffraction. The sample contained Theta-1 zeolite with estimated amount of cristobalite of less than 5%.

EXAMPLE 2 PREPARATION OF THE H-FORM THETA-1 ZEOLITE

The Theta-1 as synthesised in Example 1 which contained both $Na^+$ and $NH_4^+$ ions was directly ion exchanged in order to remove the Na+ ions. The zeolite was mixed for 1 hour with an aqueous ammonium nitrate solution (1M, zeolite to solution weight ratio of 1:20). The zeolite was filtered, washed and the ion exchange treatment repeated twice. The ammonium form of the zeolite was then dried at 100° C. and calcined overnight in air at 550° C. to convert it to the hydrogen form. The X-Ray diffraction pattern of the H-form is shown in Table 1.

EXAMPLE 3 CATALYST PREPARATION AND TESTING

The zeolite powder (H-form) was pressed into tablets at 10 tonnes. The tablets were broken and sieved into granules to pass 600 microns but not 250 micron sieves. 10 cc of the catalyst granules (weight 4.2 g) were loaded into a tubular reactor with a coaxial thermocouple well, activated in air at 550° C. and tested for the conversion of various feedstocks. Table 2A provides the product stream analysis data obtained in the conversion of methanol in the absence and presence of 1-butane. The corresponding calculated conversion values are given in Table 2B. Table 3A provides the product stream analysis data obtained in the reaction between methanol and 1-butene in the absence and presence of water. Table 3B provides the corresponding calculated conversion values.

BRIEF DESCRIPTION OF THE DRAWING

FIG. 1 illustrates the methanol conversion in the absence and presence of olefin (butene). The results clearly show the dramatic benefits obtained when butene is included as part of the feedstock. They also show the benefits of including water in the feedstock.

The terms used in the Tables are defined as follows:

| | | |
|---|---|---|
| Temperature | = | applied temperature in °C. |
| WHSV | = | weight hourly space velocity which is the weight of the oxygenate and olefins fed per weight of the catalyst per hour |
| HOS | = | hours on stream since the last air activations |
| Feed % | = | molar feed compositions |
| MeOH | = | Methanol |
| Conversion | = | carbon molar conversions % of each feed |
| Selectivities | = | carbon molar yield of each component × 100 total carbon molar conversions |
| $nC_4=$ | = | n-butenes |
| $C_1/C_2$ | = | methane, ethane and ethene |
| $C_3$ | = | propane and propene |
| $iC_4=$ | = | iso-butene |
| $C_5=$ | = | pentenes |
| Cn | = | hydrocarbons containing n carbon atoms per molecule |

TABLE 1

| XRD OF PRODUCT OF EXAMPLE 2 | | |
|---|---|---|
| 2 THETA (2θ) | D SPACINGS A° | RELATIVE INTENSITIES 100 × I/I°$_{max}$ |
| 8.17 | 10.81 | 100 |
| 10.16 | 8.70 | 22 |
| 12.81 | 6.91 | 23 |
| 16.36 | 5.42 | 11 |

TABLE 1-continued

| XRD OF PRODUCT OF EXAMPLE 2 | | |
|---|---|---|
| 2 THETA (2θ) | D SPACINGS A° | RELATIVE INTENSITIES 100 × I/I°$_{max}$ |
| 19.42 | 4.57 | 12 |
| 20.36 | 4.36 | 97 |
| 24.22 | 3.67 | 82 |
| 24.64 | 3.61 | 52 |
| 25.76 | 3.46 | 36 |

Variation in intensities of ±20%
Variation in 2θ positions of ±0.2° with corresponding variation in D spacings.
Peaks below 10% of $I_{max}$ Excluded.
Copper alpha 1 wavelengths, 1.54060.

| | |
|---|---|
| X-Ray Diffractometer | Philips PW 1820/00 |
| Slits | ¼°, 0.2°, ¼° |
| 2θ Scan | 2°–32° |
| Step Size | 0.025° |
| Time | 4 sec |

TABLE 2A

| | PRODUCT STREAM ANALYSIS | | | | | |
|---|---|---|---|---|---|---|
| HOS | 1 | 4 | 6 | 1 | 4 | 6 |
| | Feed composition (mmole/h) | | | | | |
| 1-Butene | 0.0 | 0.0 | 0.0 | 36.13 | 36.80 | 34.49 |
| Methanol | 150.00 | 150.00 | 150.00 | 150.00 | 150.00 | 150.00 |
| | Product composition (mmole/h) | | | | | |
| Methane | 0.37 | 0.61 | 0.54 | 0.80 | 0.45 | 0.43 |
| Ethane | 0.01 | 0.01 | 0.01 | 0.07 | 0.03 | 0.02 |
| Ethene | 0.08 | 0.09 | 0.06 | 2.32 | 1.66 | 1.48 |
| Propane | 0.02 | 0.02 | 0.01 | 0.87 | 0.44 | 0.32 |
| Propene | 0.07 | 0.07 | 0.06 | 8.56 | 7.35 | 6.42 |
| i-Butane | 0.01 | 0.02 | 0.02 | 1.32 | 1.37 | 1.13 |
| n-Butane | 0.01 | 0.02 | 0.02 | 1.09 | 1.99 | 1.72 |
| t-2-Butene | 0.01 | 0.01 | 0.01 | 2.27 | 1.85 | 1.10 |
| 1-Butene | 0.01 | 0.01 | 0.01 | 0.35 | 0.81 | 1.18 |
| i-Butene | 0.01 | 0.01 | 0.01 | 2.37 | 1.16 | 2.08 |
| c-2-Butene | 0.01 | 0.01 | 0.01 | 4.04 | 2.42 | 1.51 |
| C5 | 0.03 | 0.03 | 0.03 | 6.42 | 6.69 | 5.85 |
| 2-Methylbutene-2 | 0.01 | 0.01 | tr | 5.02 | 5.56 | 5.46 |
| 2-Methylbutene-1 | tr | tr | tr | 2.06 | 2.30 | 2.22 |
| 3-Methylbutene-1 | tr | tr | tr | 0.68 | 0.60 | 1.49 |
| C6 | 0.02 | 0.02 | 0.01 | 5.31 | 7.54 | 7.18 |
| C7 | tr | 0.01 | 0.02 | 2.18 | 3.05 | 3.22 |
| C8 | 0.0 | 0.0 | 0.0 | 2.92 | 2.67 | 2.88 |
| C9 | 0.0 | 0.0 | 0.0 | 1.48 | 1.19 | 1.00 |
| C10 | 0.0 | 0.0 | 0.0 | 0.73 | 0.56 | 0.51 |
| C11 | 0.0 | 0.0 | 0.0 | 0.28 | 0.23 | 0.19 |
| C12 | 0.0 | 0.0 | 0.0 | 0.14 | 0.11 | 0.09 |
| C13 | 0.0 | 0.0 | 0.0 | 0.07 | 0.05 | 0.04 |
| C14 | 0.0 | 0.0 | 0.0 | 0.04 | 0.02 | 0.02 |
| C15 | 0.0 | 0.0 | 0.0 | 0.03 | 0.02 | 0.01 |
| C16 | 0.0 | 0.0 | 0.0 | 0.02 | 0.01 | 0.01 |
| C17 | 0.0 | 0.0 | 0.0 | tr | tr | tr |
| Carbon monoxide | 0.0 | 0.0 | 0.0 | 0.10 | 0.00 | 0.00 |
| Carbon dioxide | 0.0 | 0.0 | 0.0 | 0.00 | 0.00 | 0.00 |
| Methanol | 35.38 | 38.81 | 38.02 | 0.79 | 18.94 | 16.10 |
| Formaldehyde | 0.74 | 0.67 | 0.59 | 0.00 | 0.00 | 0.00 |
| Water | 69.56 | 70.06 | 75.98 | 134.96 | 111.68 | 113.95 |
| Dimethyl ether | 51.45 | 50.43 | 54.43 | 10.23 | 12.69 | 12.81 | tr = trace (less than 0.005 detected)

TABLE 2B

| CONVERSIONS AND SELECTIVITIES | | | | | | | | | | | | |
|---|---|---|---|---|---|---|---|---|---|---|---|---|
| | | | | | | Conversion Carbon molar % | | Selectivities based on carbon molar converted | | | | |
| Temp °C. | WHSV h$^{-1}$ | HOS | MeOH | 1-Butene | *Nitrogen | MeOH | $nC_4=$ | $C_1/C_2$ | $C_3$ | $i-C_4=$ | $C_5=$ branched | $C_5=$ linear | $C_6+$ |
| 400 | 1.2 | 1 | 96 | 0 | *4 | 7.3 | — | 40.1 | 14.6 | 2.9 | 11.7 | 2.1 | 10.9 |
| 400 | 1.2 | 4 | 96 | 0 | *4 | 6.4 | — | 45.7 | 12.1 | 2.5 | 10.1 | 1.9 | 11.1 |

TABLE 2B-continued

| | | | | | | CONVERSIONS AND SELECTIVITIES | | | | | | | |
|---|---|---|---|---|---|---|---|---|---|---|---|---|---|
| | | | | | | | Conversion | | Selectivities based on carbon molar converted | | | | |
| Temp °C. | WHSV $h^{-1}$ | HOS | Feed % MeOH | 1-Butene | *Nitrogen | Carbon molar % MeOH | $nC_4=$ | $C_{1/2}$ | $C_3$ | $i$-$C_4=$ | $C_5=$ branched | $C_5=$ linear | $C_6+$ |
| 400 | 1.2 | 6 | 96 | 0 | *4 | 1.7 | — | 44.6 | 11.0 | 2.3 | 9.9 | 1.9 | 13.6 |
| 400 | 1.6 | 1 | 80.6 | 19.4 | 0 | 85.8 | 81.5 | 2.4 | 12.4 | 4.2 | 17.0 | 14.1 | 43.1 |
| 400 | 1.6 | 4 | 80.3 | 19.7 | 0 | 70.5 | 86.2 | 1.7 | 10.1 | 2.0 | 18.3 | 14.5 | 47.5 |
| 400 | 1.6 | 6 | 81.3 | 18.7 | 0 | 72.2 | 89.0 | 1.5 | 8.9 | 3.7 | 20.2 | 12.9 | 47.1 |

*Nitrogen utilised as a carrier gas for the liquid MeOH

TABLE 3A

| | PRODUCT STREAM ANALYSIS | | | | | | |
|---|---|---|---|---|---|---|---|
| HOS | 1 | 4 | 6 | 1 | 4 | 6 | 4 |
| | Feed composition (mmole/h) | | | | | | |
| 1-Butene | 16.61 | 16.98 | 16.31 | 16.09 | 16.12 | 15.98 | 627.8 |
| Methanol | 75.00 | 75.00 | 75.00 | 75.00 | 75.00 | 75.00 | 316.6 |
| Water | 0.0 | 0.0 | 0.0 | 166.67 | 166.67 | 166.67 | 1838.3 |
| | Product composition (mmole/h) | | | | | | |
| Methane | 0.27 | 0.13 | 0.15 | 0.23 | 0.16 | 0.06 | 0.77 |
| Ethane | 0.01 | 0.01 | 0.01 | 0.0 | 0.0 | 0.0 | 0.06 |
| Ethene | 0.10 | 0.08 | 0.10 | 0.17 | 0.19 | 0.14 | 2.52 |
| Propane | 0.09 | 0.06 | 0.08 | 0.06 | 0.04 | 0.03 | 1.03 |
| Propene | 0.55 | 0.44 | 0.61 | 0.63 | 0.53 | 0.57 | 22.18 |
| i-Butane | 0.22 | 0.15 | 0.24 | 0.15 | 0.12 | 0.13 | 0.97 |
| n-Butane | 0.94 | 0.70 | 1.14 | 0.97 | 0.79 | 0.61 | 12.56 |
| t-2-Butene | 1.25 | 1.68 | 2.32 | 9.13 | 9.26 | 10.37 | 150.05 |
| 1-Butene | 0.58 | 0.32 | 0.89 | 3.88 | 3.70 | 4.30 | 104.09 |
| i-Butene | 1.39 | 1.04 | 1.73 | 1.76 | 1.47 | 1.56 | 87.22 |
| c-2-Butene | 0.88 | 0.85 | 1.37 | 6.04 | 6.33 | 6.84 | 112.70 |
| C5 | 1.89 | 1.78 | 2.36 | 0.51 | 0.64 | 0.47 | 19.15 |
| 2-Methyl-butene-2 | 4.56 | 3.34 | 5.76 | 1.36 | 1.93 | 1.33 | 30.87 |
| 2-Methyl-butene-1 | 1.27 | 1.60 | 1.77 | 0.48 | 0.61 | 0.44 | 13.41 |
| 3-Methyl-butene-1 | 0.57 | 0.55 | 0.57 | 0.14 | 0.19 | 0.13 | 2.21 |
| C6 | 3.09 | 3.08 | 2.98 | 0.19 | 0.31 | 0.23 | 4.85 |
| C7 | 1.01 | 0.99 | 0.79 | 0.05 | 0.06 | 0.10 | 3.83 |
| C8 | 0.56 | 0.70 | 0.61 | 0.0 | 0.0 | 0.0 | 19.05 |
| C9 | 0.39 | 0.58 | 0.54 | 0.0 | 0.0 | 0.0 | 5.60 |
| C10 | 0.22 | 0.32 | 0.29 | 0.0 | 0.0 | 0.0 | 1.80 |
| C11 | 0.12 | 0.14 | 0.12 | 0.0 | 0.0 | 0.0 | 0.38 |
| C12 | 0.05 | 0.05 | 0.05 | 0.0 | 0.0 | 0.0 | 0.13 |
| C13 | 0.02 | 0.02 | 0.02 | 0.0 | 0.0 | 0.0 | 0.02 |
| C14 | 0.01 | 0.01 | 0.01 | 0.0 | 0.0 | 0.0 | 0.0 |
| C15 | tr | tr | tr | 0.0 | 0.0 | 0.0 | 0.0 |
| C16 | 0.0 | 0.0 | 0.0 | 0.0 | 0.0 | 0.0 | 0.0 |
| C17 | 0.0 | 0.0 | 0.0 | 0.0 | 0.0 | 0.0 | 0.0 |
| Carbon monoxide | 0.0 | 0.0 | 0.0 | 0.0 | 0.0 | 0.0 | 0.0 |
| Carbon dioxide | 0.0 | 0.0 | 0.0 | 0.0 | 0.0 | 0.0 | 0.0 |
| Methanol | 9.23 | 9.61 | 10.47 | 30.34 | 31.05 | 32.44 | 178.14 |
| Formaldehyde | 0.0 | 0.0 | 0.0 | 0.0 | 0.0 | 0.0 | 0.0 |
| Water | 53.25 | 43.08 | 47.27 | 225.4 | 219.64 | 210.82 | 2008.76 |
| Dimethyl ether | 12.12 | 17.86 | 15.86 | 0.0 | 0.0 | 0.0 | 18.05 | tr = trace (less than 0.005 detected)

EXAMPLE 4: HIGH SPACE VELOCITY 15 grams of H-Theta-1 zeolite granules as prepared in Example 3 were packed into a tubular reactor. Nitrogen was passed at the rate of 60 cc/minute and the temperature was raised to 550° C. over 6 hours. Water was continuously injected over the catalyst at the rate of 30 cc/hour for two hours at 550° C. 10 grams of the steamed catalyst were refluxed in 200 cc of 1 equivalent/liter nitric acid. The zeolite was filtered, washed and the acid treatment at reflux was repeated twice more. The zeolite was finally dried and pressed into granules as described above. The granules were loaded into a reactor and tested as described in Example 3.

The product composition given was that obtained after 4 hours on stream since the previous regeneration step. Regeneration was carried out as follows: At the conclusion of a run (usually 6.5 hours on stream) the feed was turned off and the reactor was depressurised to ambient. The catalyst was purged with nitrogen (10 cc/min measured at 5 barg) for 30 minutes. During this purge step the reactor was cooled to 350° C. In addition to the nitrogen flow air was introduced at 20 cc/min (measured at 2 barg). The temperature was ramped up at 5° C./minute. The temperature was held for 2 hours at 450°, 500° and 550° C. and for 4 hours at 580° C. The reactor was then cooled to 350° C. and purged in nitrogen ready for the following test run.

The feed was started and the temperature and pressure were then adjusted to the run conditions.

TABLE 4A

| PRODUCT STREAM ANALYSIS | | |
|---|---|---|
| Feed composition (mmole/h) | | |
| Temperature °C. | 400 | 408 |
| HOS | 4 | 4 |
| 1-Butene | 1421 | 1265 |
| Methanol | 359 | 629 |
| Nitrogen | 3771 | 3697 |
| Product composition (mmole/h) | | |
| Methane | 2.98 | 4.16 |
| Ethane | 0.00 | 0.00 |
| Ethene | 3.68 | 3.48 |
| Propane | 3.41 | 2.23 |

TABLE 3B

| | | | | | | CONVERSIONS AND SELECTIVITIES | | | | | | | |
|---|---|---|---|---|---|---|---|---|---|---|---|---|---|
| | | | | | | | Conversion | | Selectivities based on carbon molar converted | | | | |
| Temp °C. | WHSV $h^{-1}$ | HOS | Feed % MeOH | 1-Butene | Water | Carbon molar % MeOH | $nC_4=$ | $C_{1/2}$ | $C_3$ | $i$-$C_4=$ | $C_5=$ branched | $C_5=$ linear | $C_6+$ |
| 300 | 0.8 | 1 | 82 | 18 | 0 | 55.4 | 83.7 | 0.5 | 2.0 | 5.9 | 34.0 | 10.1 | 40.6 |
| 300 | 0.8 | 4 | 82 | 18 | 0 | 39.6 | 83.2 | 0.3 | 1.7 | 4.8 | 31.5 | 10.2 | 48.4 |
| 300 | 0.8 | 6 | 82 | 18 | 0 | 43.8 | 71.9 | 0.4 | 2.2 | 7.3 | 42.9 | 12.5 | 40.7 |
| 300 | 0.7 | 1 | 29.0 | 6.4 | 64.6 | 59.5 | −18.4 | 1.8 | 6.5 | 22.2 | 34.1 | 5.1 | 4.8 |
| 300 | 0.7 | 4 | 29.0 | 6.4 | 64.6 | 58.6 | −19.7 | 1.7 | 5.5 | 18.9 | 47.0 | 6.9 | 7.4 |
| 300 | 0.7 | 6 | 29.0 | 6.4 | 64.6 | 56.7 | −34.6 | 1.6 | 8.3 | 29.4 | 48.6 | 7.4 | 9.9 |
| 414 | 20.9 | 4 | 11.3 | 22.6 | 66.1 | 32.3 | 41.6 | 0.6 | 6.4 | 32.0 | 21.3 | 8.8 | 26.0 |

− sign means n-butenes formed to a level exceeding the quantity fed

TABLE 4A-continued

| PRODUCT STREAM ANALYSIS | | |
|---|---|---|
| Propene | 58.23 | 46.35 |
| i-Butane | 3.02 | 2.32 |
| n-Butane | 33.98 | 25.35 |
| t-2-Butene | 260.94 | 263.77 |
| 1-Butene | 177.11 | 176.42 |
| i-Butene | 246.00 | 197.99 |
| c-2-Butene | 198.00 | 196.18 |
| 2-Methylbutene-2 | 149.82 | 145.73 |
| 2-Methylbutene-1 | 61.67 | 61.61 |
| 3-Methylbutene-1 | 9.13 | 9.47 |
| C5 | 81.04 | 82.45 |
| C6 | 29.29 | 34.77 |
| C7 | 15.16 | 11.48 |
| C8 | 42.98 | 25.73 |
| C9 | 2.13 | 0.00 |
| C10 | 1.36 | 0.00 |
| C11 | 0.55 | 0.00 |
| C12 | 0.37 | 0.00 |
| C13 | 0.15 | 0.00 |
| C14 | 0.04 | 0.00 |
| C15 | 0.00 | 0.00 |
| C16 | 0.00 | 0.00 |
| C17 | 0.00 | 0.00 |
| Carbon monoxide | 0.00 | 0.00 |
| Carbon dioxide | 0.00 | 2.77 |
| Water | 305.59 | 506.05 |
| Formaldehyde | 0.00 | 0.00 |
| Methanol | 14.73 | 79.78 |
| Dimethyl ether | 4.41 | 17.30 |
| Hydrogen | 0.00 | 0.00 |

TABLE 4B

| | | | | | | CONVERSIONS AND SELECTIVITIES | | | | | | | |
|---|---|---|---|---|---|---|---|---|---|---|---|---|---|
| | | | | | | | Conversion | | Selectivities based on carbon molar converted | | | | |
| Temp | WHSV | | | Feed % | | | Carbon molar % | | | | | $C_5=$ | $C_5=$ |
| °C. | $h^{-1}$ | HOS | MeOH | 1-Butene | Nitrogen | MeOH | $nC_4=$ | $C_1/_2$ | $C_3$ | $i-C_4=$ | branched | linear | $C_6+$ |
| 400 | 20 | 4 | 6.4 | 25.6 | 68.0 | 99.6 | 55.2 | 0.29 | 5.27 | 28.06 | 31.46 | 11.55 | 19.15 |
| 408 | 20 | 4 | 11.3 | 22.6 | 66.1 | 97.7 | 49.7 | 0.45 | 4.77 | 25.94 | 35.50 | 13.50 | 8.63 |

We claim:

1. A process for the production of olefins which comprises passing an oxygenate-containing feedstock over a zeo-type catalyst at a temperature greater than 200° C. wherein the oxygenate-containing feedstock comprises $C_3$ and/or $C_4$ olefins, the oxygenate is at least one of methanol, formaldehyde or dimethylether, the molar ratio of olefin to oxygenate being greater than 1:20, and the zeo-type catalyst is of a TON-type structure and is selected from the group consisting of aluminosilicates, gallosilicates, zincosilicates, borosilicates, titanosilicates, aluminogermanates, gallogermanates, zincogermanates, borogermanates and titanogermanates.

2. A process according to claim 1, in which the oxygenate is methanol.

3. A process according to claim 1, in which the molar ratio of olefin to oxygenate in the feedstock is greater than 1:4.

4. A process according to claim 1, in which the TON-type catalyst is an aluminosilicate.

5. A process according to claim 1, in which the TON-type catalyst is used in the hydrogen form.

6. A process according to claim 1, in which the reaction temperature is in the range of from 250° to 600° C.

7. A process according to claim 1, in which the reaction is carried out at a pressure of from 2 to 10 bar absolute.

8. A process according to claim 1, in which the reaction is carried out at a WHSV of from 0.10 to 1000 per hour.

* * * * *